(12) United States Patent
Rivera et al.

(10) Patent No.: US 6,646,130 B2
(45) Date of Patent: Nov. 11, 2003

(54) PROCESS TO CHIRAL INTEGRIN ANTAGONIST BETA-AMINO ACID INTERMEDIATE

(75) Inventors: Nelo R. Rivera, New Milford, NJ (US); Christopher J. Welch, Cranbury, NJ (US); Yi Xiao, Fanwood, NJ (US); Nobuyoshi Yasuda, Mountainside, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/197,003

(22) Filed: Jul. 17, 2002

(65) Prior Publication Data

US 2003/0045555 A1 Mar. 6, 2003

Related U.S. Application Data

(60) Provisional application No. 60/306,502, filed on Jul. 19, 2001.

(51) Int. Cl.[7] .................. C07D 213/38; C07D 213/46; A61K 31/4412
(52) U.S. Cl. ................ 546/301; 546/300; 514/351
(58) Field of Search ................ 546/300, 301; 514/351

(56) References Cited

U.S. PATENT DOCUMENTS 6,017,926 A   1/2000   Askew et al.

FOREIGN PATENT DOCUMENTS

WO   WO 01/34602   5/2001

OTHER PUBLICATIONS

S.G. Davies et al., Tetrahedron: Asymmetry, vol. 2, No. 3, pp. 183–186 (1991).*

S. G. Davies et al., Tetrahedron: Asymmetry vol. 2, No.3, pp.183–186 (1991).

H. Marlon Zhong et al., Tetrahedron Letters 40 pp. 7721–7725 (1999).

* cited by examiner

*Primary Examiner*—Alan L. Rotman
*Assistant Examiner*—Janet L Coppins
(74) *Attorney, Agent, or Firm*—Patricia A. Shatynski; Mark R. Daniel

(57) ABSTRACT

The invention discloses a novel process for the preparation of enantiomerically enriched mixtures of compounds of structural formula I which are useful intermediates in the synthesis of αvβ3 integrin receptor antagonists

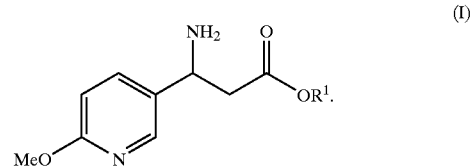

(I)

8 Claims, No Drawings

PROCESS TO CHIRAL INTEGRIN ANTAGONIST BETA-AMINO ACID INTERMEDIATE

CROSS-REFERENCE TO RELATED APPLICATIONS

The present invention is related to U.S. provisional application Serial No. 60/306,502, filed Jul. 19, 2001, the contents of which are hereby incorporated by reference in their entirety.

BACKGROUND OF THE INVENTION

U.S. Pat. No. 6,017,926 (issued Jan. 25, 2000) discloses compounds of the structural formula:

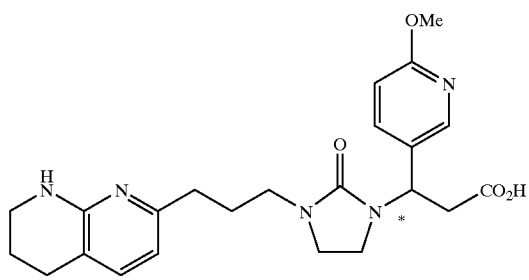

which include the two enantiomeric forms at the C-3 position (marked with an *) of the right-hand propionic acid side-chain.

These compounds are antagonists of the integrin receptor αvβ3 and are therefore useful for inhibiting bone resorption, restenosis, angiogenesis, diabetic retinopathy, macular degeneration, inflammatory arthritis, cancer, and metastatic tumor growth. They are particularly useful for inhibiting bone resorption and for the treatment and prevention of osteoporosis.

Processes for the preparation of the enantiomerically enriched (R) and (S) forms of the above compound are disclosed in U.S. Pat. No. 6,017,926 and WO 01/34602. A key intermediate in these published processes is enantiomerically enriched 3(S)- or 3(R)-(6-methoxy-pyridin-3-yl)-β-alanine methyl, ethyl or tert-butyl ester of structural formulae (1) and (2), respectively.

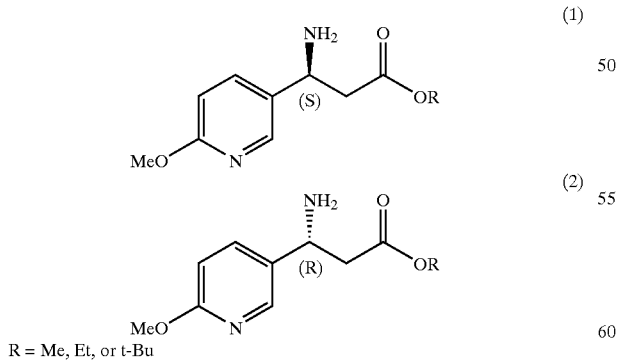

R = Me, Et, or t-Bu

The published chemical routes to the above chiral β-amino acids involve a diastereoselective Michael addition of the lithium amide derived from N-benzyl-(S)- or (R)-2-methylbenzylamine using conditions described by Davies et al., in *Tetrahedron: Asymmetry*, Vol. 2, pp. 183–186, 1991. However, this methodology suffers from economic disadvantages associated with the high costs of reagents in the Davies chemistry and from operational limitations in the diastereoselective Michael addition reaction. The present invention is concerned with a short and efficient route to enantiomerically enriched mixtures of alkyl esters of 3-(6-methoxy-pyridin-3-yl)-β-alanine which employs a chiral resolution by crystallization.

SUMMARY OF THE INVENTION

The present invention encompasses a process for the preparation of enantiomerically enriched mixtures of alkyl esters of 3-(6-methoxy-pyridin-3-yl)-β-alanine which are useful in the synthesis of integrin αvβ3 antagonists. Another aspect of the present invention is concerned with novel salts of 3-(6-methoxy-pyridin-3-yl)-β-alanine alkyl esters and a enantiomerically enriched N-protected-α-amino acid.

DETAILED DESCRIPTION OF THE INVENTION

One aspect of the present invention is concerned with a process for the preparation of enantiomerically enriched mixtures of compounds of structural I:

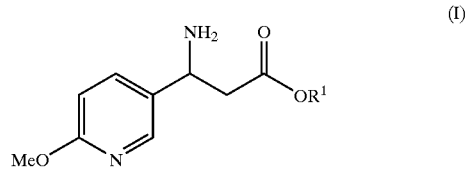

wherein
R$^1$ is C$_{1-4}$ alkyl;
comprising the steps of:
(a) mixing a compound of structural formula I with an (R)- or (S)-amino acid of structural formula II:

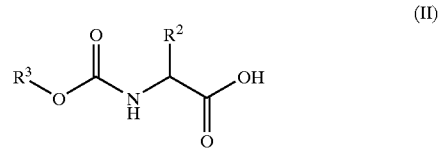

wherein R$^2$ is selected from the group consisting of phenyl, benzyl, 1-naphthylmethyl, 2-naphthylmethyl, 4-imidazolylmethyl, and 4-hydroxybenzyl; and and R$^3$ is tert-butyl, benzyl or 9-fluorenylmethyl; in an alcohol solvent system;
(b) heating the mixture from about 10° C. to about 100° C.;
(c) allowing the mixture to cool so that a crystalline (R)- or (S)-amino acid salt of said compound of formula I is formed;
(d) filtering the mixture to separate the crystalline salt from the supernatant; and
(e) liberating said compound of formula I from the crystalline salt by treating the salt with a base.

In one embodiment of this aspect of the present invention, R$^1$ is methyl, ethyl, or tert-butyl. In a second embodiment, R$^2$ is benzyl. In a third embodiment, R$^3$ is benzyl. In a class of the first embodiment, both R$^2$ and R$^3$ represent benzyl.

In a further embodiment, the amino acid used in Step (a) is N-(benzyloxycarbonyl)-(S)-phenylalanine.

In yet a further embodiment the alcohol solvent system is about 0% to about 50% water in an alcohol selected from the group consisting of methanol, ethanol, and isopropanol. In a class of this embodiment the alcohol solvent system is aqueous ethanol or aqueous methanol.

The racemic amino ester for the chiral resolution step can be prepared as described in Scheme 1.

SCHEME 1

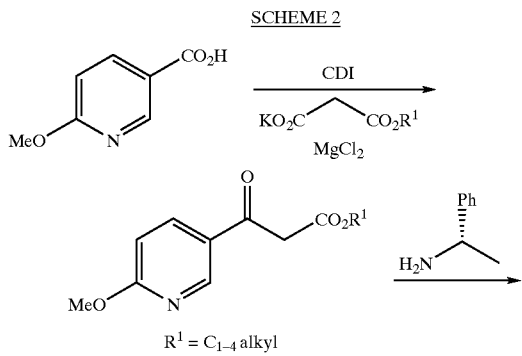

A partially enantiomerically enriched amino ester for further chiral resolution can be prepared as described in Scheme 2. This route is based on a published method for methyl 3-amino-3-(3-pyridyl)-propanoate [H. M. Zhong, et al., *Tetrahedron Lett.*, 40: 7721–7725 (1999)].

SCHEME 2

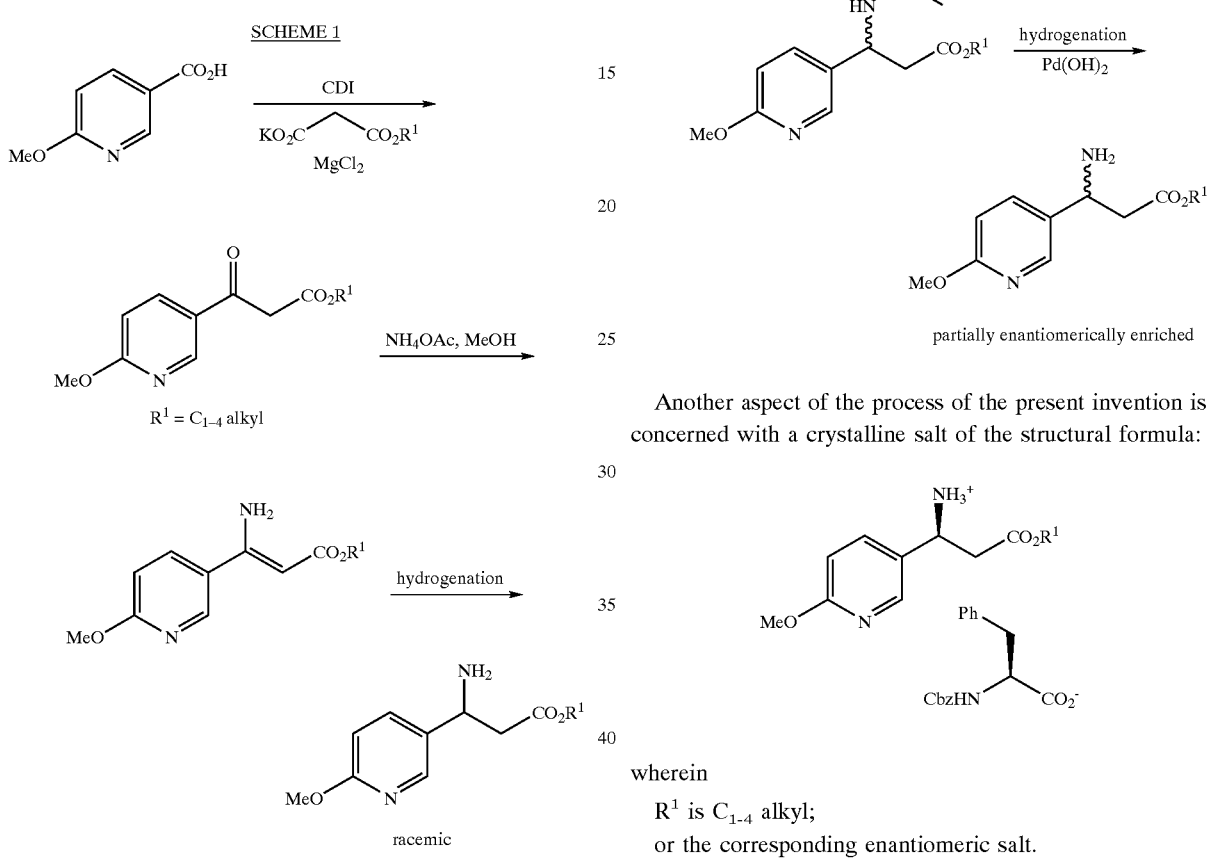

Another aspect of the process of the present invention is concerned with a crystalline salt of the structural formula:

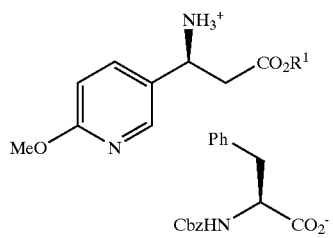

wherein $R^1$ is $C_{1-4}$ alkyl;

or the corresponding enantiomeric salt.

In one embodiment of this aspect, $R^1$ is methyl.

The term "enantiomerically enriched" is intended to include compounds that are enantiomerically pure.

The term "% enantiomeric excess" (abbreviated "ee") shall mean the % major enantiomer less the % minor enantiomer. Thus, an 80% enantiomeric excess corresponds to formation of 90% of one enantiomer and 10% of the other. The term "enantiomeric excess" is synonymous with the term "optical purity."

The term "Cbz" represents "benzyloxycarbonyl."

Representative experimental procedures utilizing the novel process of the present invention are detailed below. For purposes of illustration, the following Examples are directed to the preparation of enantiomerically enriched mixtures of 3(S)-(6-methoxy-pyridin-3-yl)-β-alanine methyl ester, but doing so is not intended to limit the present invention to a process for making those specific mixtures.

The differential scanning calorimeter (DSC) curve was taken on a TA 2910 Differential Scanning Calorimeter with a heating rate of 10° C./minute under nitrogen.

X-ray powder diffraction patterns were generated on a Philip Analytical X-ray diffractometer using Cu Kα radiation. The experiments were run at ambient condition.

EXAMPLE 1

Step A:

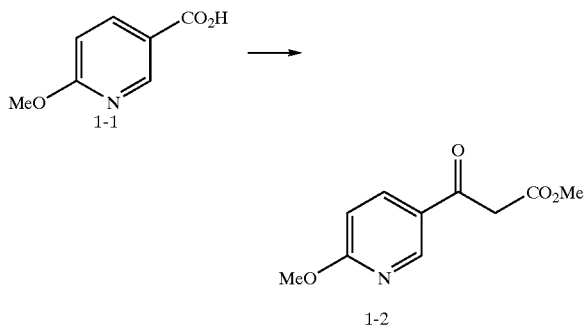

To a solution of 6-methoxynicotinic acid (1-1) (50.0 g, 327 mmol) in acetonitrile (500 mL) was added 1,1'-carbonyldiimidazole (58.3 g, 359 mmol) portionwise over 5 minutes at room temperature. The resulting slurry solution was aged for 45 min at room temperature.

Simultaneously, to a cooled solution of mono-methyl malonate potassium salt (76.7 g, 490 mmol) and MgCl$_2$ (35.0 g, 359 mmol) in acetonitrile (1000 mL) was added triethylamine (137 mL, 980 mmol) slowly such that the maximum internal temperature was less than 10° C. After the addition was complete, the mixture was allowed to warm to room temperature and maintained there for 45 min. The contents of the activated nicotinic acid was added to the malonate solution at room temperature which was then aged at 40° C. for several hours until reaction was complete. The reaction mixture was then cooled to 5° C. and the pH was adjusted to 6.5 with 3 N HCl (570 mL) while maintaining maximum temperature of 15° C. The organic layer was separated and the aqueous layer was re-extracted with EtOAc (2×250 mL). The combined organic layers were concentrated under reduced pressure to a thick slurry and water (100 mL) was added to the slurry. The resulting solid was filtered, washed with H$_2$O (2×50 mL) and dried under vacuum to give 60 g of ketoester 1-2 as a white solid; mp 75–77° C.

$^1$H NMR (CDCl$_3$, 400 MHz): δ 12.52 (s, 1H); 8.62 (dd, J=2.6, 0.7 Hz, 1H); 7.92 (dd, J=8.8, 2.6 Hz, 1H); 6.78 (dd, J=8.8, 0.7 Hz, 1H); 5.59 (s, 1H); 3.99 (s, 3H); 3.81 (s, 3H).

$^{13}$C NMR (CDCl$_3$, 101 MHz): δ 173.3, 169.6, 165.9, 145.8, 136.1, 122.6, 110.8, 86.2, 53.9, 51.4.

Step B:

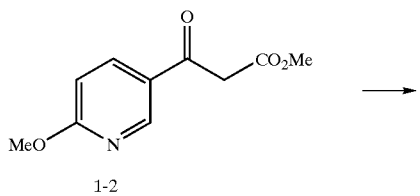

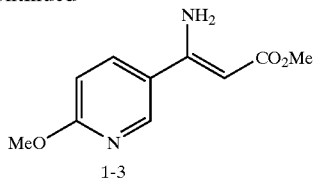

A mixture of keto ester 1-2 (30.0 g, 144 mmol) and ammonium acetate (22.2 g, 288 mmol) in ethanol (300 mL) was heated overnight at 65° C. After the reaction was complete, the mixture was cooled to room temperature and was used directly for the hydrogenation step without further purification. The enamine 1-3 was isolated as follows. The reaction mixture was concentrated under reduced pressure. The residue was dissolved in a mixture of EtOAc and water. The organic layer was dried with magnesium sulfate and concentrated under reduced pressure. The enamine 1-3 was obtained as a white solid; mp 67–69° C.

Enamine 1-3 can also be prepared using ammonium formate in place of ammonium acetate. A mixture of keto ester 1-2 (50.0 g, 240.4 mmol) and ammonium formate (75.8 g, 1202 mmol) in methanol (500 mL) was heated to 65° C. and held overnight. After the reaction was complete as determined by HPLC assay, one half of the solution was concentrated under vacuum. The solids were taken up in EtOAc (250 mL) and washed with aqueous sodium bicarbonate solution (100 mL). After phase separation, the aqueous solution was re-extracted with EtOAc (100 mL). The combined organic layers were concentrated under vacuum to give 25.0 g of material at 95 wt % purity (HPLC assay), corrected yield of 95%.

$^1$H NMR (CDCl$_3$, 400 MHz): δ 8.38 (dd, J=2.7, 0.6 Hz, 1H); 7.71 (dd, J=8.8, 2.7 Hz, 1H); 6.77 (dd, J=8.8, 0.6 Hz, 1H); 4.92 (s, 1H); 3.97 (s, 3H); 3.71 (s, 3H).

$^{13}$C NMR (CDCl$_3$, 101 MHz): δ 170.5, 165.4, 157.7, 144.9, 136.5, 126.6, 111.0, 84.3, 53.8, 50.5.

Step C:

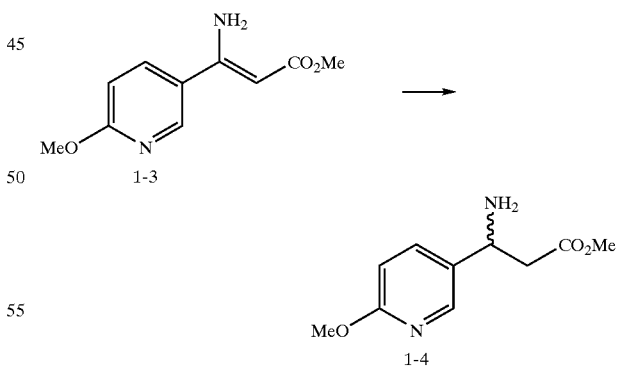

The enamine solution from Step B (96 mmol in 200 mL ethanol) was hydrogenated in the presence of Pd(OH)$_2$-on-carbon (20 wt %; 3 g) under 40 psi of hydrogen gas pressure at room temperature overnight. The catalyst was removed by filtering through solka flok, and the solvent was switched to EtOAc (150 mL). The solution was washed with saturated sodium bicarbonate solution (100 mL). The aqueous layer was re-extracted with dichloromethane (2×50 mL). The combined organic layers were dried over sodium sulfate and concentrated under vacuum to give 17.7 g of amino ester 1-4 as an oil.

Amino ester 1-4 can also be prepared using ammonium formate. The enamine 1-3 (10 g, 48 mmol) was dissolved in MeOH (100 mL) then degassed and purged with nitrogen. To this was added ammonium formate (12.1 g, 192 mmol) and 5% Pd/C (1.0 g) and stirred at room temperature over 48 hours. After the reaction was complete, the catalyst was removed by solka flok filtration. An aliquot (one fourth) was taken up and processed as follows. The methanolic solution was concentrated under vacuum to an oil then taken up in $CH_2Cl_2$ (50 mL) and washed with aqueous sodium bicarbonate solution (25 mL). After phase separation, the organic layer was re-extracted with in $CH_2Cl_2$ (50 mL). The combined organic layers were dried over $MgSO_4$, filtered and concentrated under vacuum to give an oil (2.50 g).

$^1$H NMR (CDCl$_3$, 400 MHz): δ 8.12 (d, J=2.5 Hz, 1H); 7.61 (dd, J=8.6, 2.5 Hz, 1H); 6.72 (d, J=8.6 Hz, 1H); 4.41 (m, 1H); 3.92 (s, 3H); 3.68 (s, 3H); 2.64 (m, 2H); 1.79 (bs, 2H).

$^{13}$C NMR (CDCl$_3$, 101 MHz): δ 172.1, 163.7, 144.8, 136.8, 132.5, 110.9, 53.4, 51.7, 49.8, 43.6.

Step D:

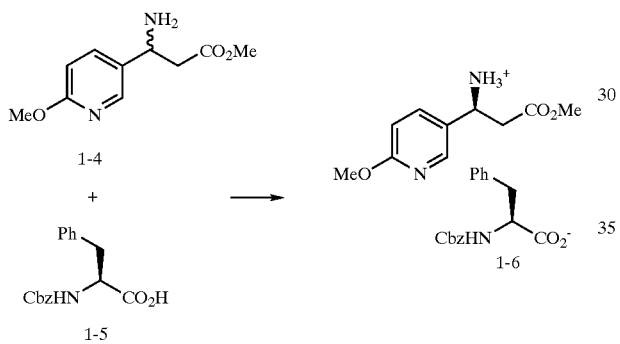

The racemic amine 1-4 from Step C (4.0 g, 19 mmol) was dissolved in aqueous ethanol solution (28.4 mL 5% $H_2O$/EtOH). To this solution was added N-Cbz-(S)-phenylalanine (1-5) (5.7 g, 19 mmol) dissolved in 5% $H_2O$/EtOH (28.4 mL). The reaction mixture was optionally seeded and aged overnight. The suspension was then filtered, and the solids were washed with 5% $H_2O$/EtOH (2×5 mL) to give 4.4 g of the crystalline salt 1-6. The recovered crystalline salt had an enantiomeric excess of 94% as determined by chiral HPLC under the indicated conditions given below. The salt can be recrystallized from the same solvent system to provide additional enantiomeric enrichment.

$^1$H NMR (CD$_3$OD, 400 MHz): δ 8.18 (d, J=2.4 Hz, 1H), 7.74 (dd, J=8.4 and 2.4 Hz, 1H), 7.33–7.11 (m, 10H), 6.87 (d, J=8.4 Hz, 1H), 5.02 (d, J=12.5 Hz, 1H), 4.95 (d, J=12.5 Hz, 1H), 4.61 (t, J=7.4 Hz, 1H), 4.28 (dd, J=7.6, 4.8 Hz, 1H), 3.89 (s, 3H), 3.65 (s, 3H), 3.16 (dd, J=14.1, 4.8 Hz, 1H), 3.02 (dd, J=16.9, 7.4 Hz, 1H), 2.91 (dd, J=16.9, 7.4 Hz, 1H), and 2.89 (dd, J=14.1, 7.6 Hz).

$^{13}$C NMR (CDCl$_3$, 101 MHz): δ 174.4, 170.9, 163.6, 156.0, 146.2, 139.0, 138.3, 137.6, 129.8, 129.6, 128.6, 128.3, 128.0, 127.8, 126.4, 110.6, 65.4, 56.8, 53.5, 51.9, 49.2, 40.7, 37.5.

The crystalline salt obtained was also characterized by a differential scanning calorimetry curve, at a heating rate of 10° C./min. under nitrogen in an open pan, exhibiting a sharp melting endotherm with a peak temperature of about 148° C. (extrapolated onset temperature of about 147° C. and an enthalpy of 149 J/g). The X-ray powder diffraction showed absorption bands at spectral d-spacings of 3.5, 3.6, 3.8, 4.2, 7.6, 9.3, 11.3, and 15.2 angstroms.

EXAMPLE 2

Step A:

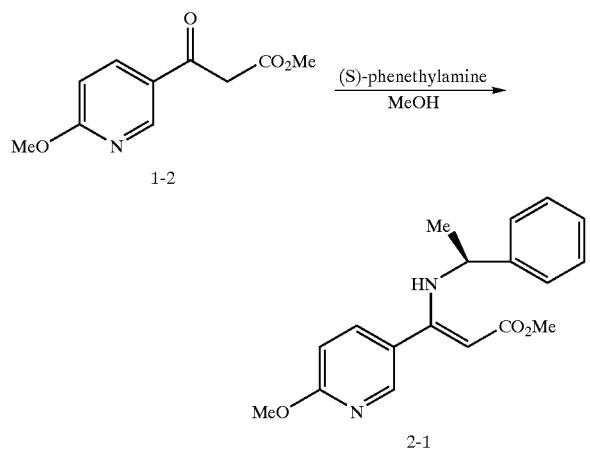

A solution of keto ester 1-2 (19.2 g), (S)-(-)-1-phenylethylamine (16.8 g) in 10% acetic acid/toluene (120 mL) was heated to reflux temperature under 70 torr vacuum using a Dean Stark trap to remove water as it formed. After 24 hours, the reaction mixture was cooled to 5° C. and the pH adjusted to 6.8 with 5% NaHCO$_3$. The aqueous layer was extracted with 200 ml of isopropyl acetate. The organic layer was washed with 100 ml water, dried (MgSO$_4$), filtered and evaporated to give a thick oil that slowly crystallized upon standing; 25.9 grams of 2-1 was recovered. The solid was recrystallized from 50 ml hexanes; m.p. 48.4–48.9° C.

$^1$H NMR (CDCl$_3$, 400 MHz): δ 8.87 (d, J=9.2 Hz, 1H); 8.02 (d, J=2.4 Hz, 1H); 7.39 (dd, J=8.4, 2.4 Hz, 1H); 7.26 (m, 2H); 7.19 (m, 1H); 7.08 (m, 2H); 6.63 (d, J=8.4 Hz, 1H); 4.62 (s, 1H); 4.42 (dq, J=9.2, 6.8 Hz, 1H); 3.93 (s, 3H); 3.71 (s, 3H); 1.48 (d, J=6.8 Hz, 3H).

$^{13}$C NMR (CDCl$_3$, 101 MHz): δ 170.4, 164.4, 161.1, 145.8, 144.5, 137.9, 128.5, 127.0, 125.4, 125.3, 110.2, 86.9, 54.0, 53.5, 50.3, 24.6.

Step B:

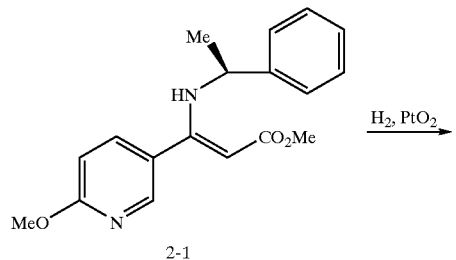

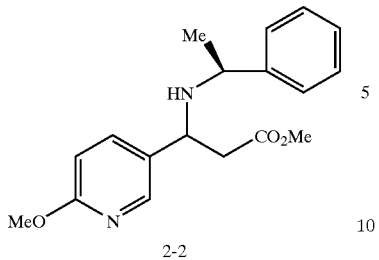

2-2

Enamine 2-1 (25.9 g) in 10% AcOH/MeOH (260 mL) was hydrogenated in the presence of platinum oxide (2.59 g) at 15 psi H₂ and room temperature for 15 hours. The catalyst was removed by filtration through solka floc and washed with MeOH. The 3:1 solution of diastereoisomers was used directly in Step C below. A sample for NMR analysis was prepared by evaporation of the methanol. The resultant oil contained a 0.5 mole of acetic acid.

Major Diastereoisomer (As Acetate Salt)

$^1$H NMR (CDCl$_3$, 400 MHz): δ 7.89 (d, J=2.4 Hz, 1H); 7.57 (dd, J=8.4, 2.4 Hz, 1H); 7.34 (m, 2H); 7.27 (m, 1H); 7.20 (m, 2H); 6.75 (d, J=8.4 Hz, 1H); 4.90 (br s, 2H); 3.94 (s, 3H); 3.77 (dd, J=8.8, 5.0 Hz, 1H); 3.63 (s, 3H); 3.43 (q, J=6.6 Hz, 1H); 2.74 (dd, J=16.0, 5.0 Hz, 1H); 2.53 (dd, J=16.0, 8.8 Hz, 1H); 2.08 (s, 3H); 1.27 (d, J=6.6 Hz, 3H).

$^{13}$C NMR (CDCl$_3$, 101 MHz): δ 175.7, 171.8, 163.8, 146.0, 144.1, 137.5, 129.8, 128.5, 127.2, 126.6, 111.1, 54.9, 53.4, 51.6, 42.2, 24.6, 21.2.

Minor Diastereoisomer (As Acetate Salt)

$^1$H NMR (CDCl$_3$, 400 MHz): δ 8.02 (d, J=2.4 Hz, 1H); 7.53 (dd, J=8.4, 2.4 Hz, 1 H); 7.26 (m, 2H); 7.20 (m, 3H); 6.67 (d, J=8.4 Hz, 1H); 4.90 (br s, 2H); 4.17 (t, J=7.0 Hz, 1H); 3.91 (s, 3H); 3.71 (q, J=6.2 Hz, 1H); 3.62 (s, 3H); 2.78 (dd, J=1.56, 7.0 Hz, 1H); 2.65 (dd, J=15.6, 7.0 Hz, 1H); 2.08 (s, 3H); 1.38 (d, J=6.2 Hz, 1H).

$^{13}$C NMR (CDCl$_3$, 101 MHz): δ175.7, 171.7, 163.6, 145.7, 145.0, 137.3, 130.3, 128.4, 127.0, 126.5, 110.9, 55.1, 54.1, 53.4, 51.6, 41.6, 22.3, 21.2.

Step C:

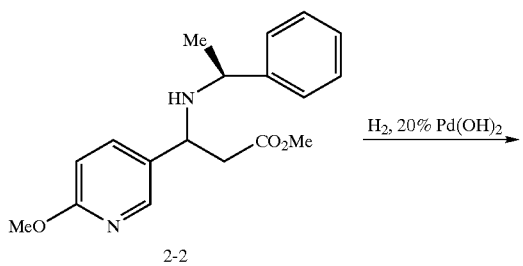

2-2

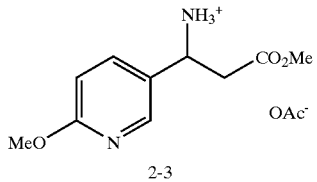

2-3

Amino ester 2-2 (25.9 g) in 10% AcOH/MeOH (260 mL) was hydrogenated in the presence of 20% palladium hydroxide at 40 psi H₂ and 35° C. for hours. The catalyst was removed by filtration through solka floc and washed with MeOH. The solution was evaporated, and the resulting oil was used directly in Step D below. The acetate salt crystallized upon standing; m.p. 100.2–101.4° C.

$^1$H NMR (CDCl$_3$, 400 MHz): δ8.13 (d, J=2.4 Hz, 1H); 7.64 (dd, J=9.0, 2.4 Hz, 1H); 6.74 (d, J=9.0 Hz, 1H); 4.90 (br s, 3H); 4.44 (dd, J=8.8, 5.0 Hz, 1H); 3.92 (s, 3H); 3.67 (s, 3H); 2.79 (dd, J=16.2, 8.8 Hz, 1H); 2.67 (dd, J=16.2, 5.0 Hz, 1H); 2.02 (s, 3H)

$^{13}$C NMR (CDCl$_3$, 101 MHz): δ175.8, 171.8, 153.9, 145.0, 136.9, 131.1, 111.0, 53.4, 51.8, 49.6, 42.4, 21.3.

Step D:
Chiral Resolution of Enantiomerically Enhanced β-Amino Ester 2-3

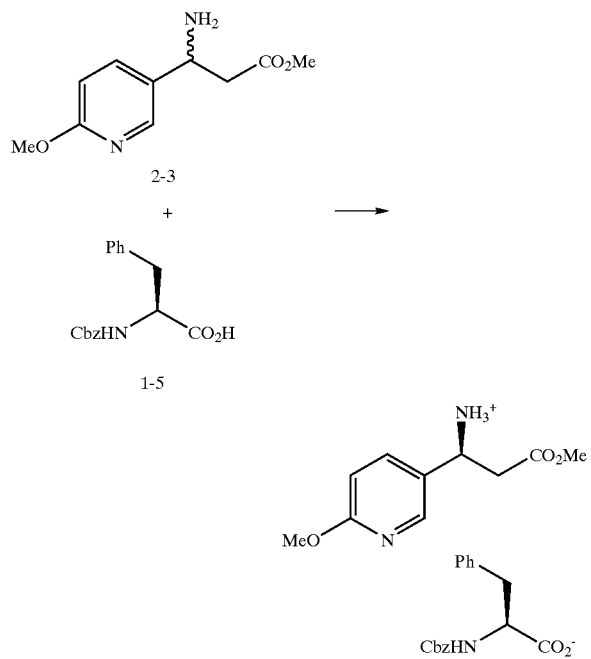

The enantiomerically enriched amino ester (53% ee, 2.0 g, 9.5 mmol) was dissolved in aqueous ethanol solution (14.2 mL 5% H₂O/EtOH) and seeded. To this solution was added slowly N-Cbz-(S)-phenylalanine (2.85 g, 9.5 mmol) dissolved in 5% H₂O/EtOH (14.2 mL). The internal temperature was maintained at room temperature during the addition period. The slurry was aged overnight at room temperature, filtered, and the solids washed with 5% H₂O/EtOH (2×5 mL) to give 2.864 g (92.5% recovery) of the crystalline salt 1-6. The recovered crystalline salt had an enantiomeric excess of 98% as determined by chiral HPLC under the indicated conditions given below.

HPLC Assay Condition

Determination of Enantiomeric Excess

Enantiomeric excess was determined using a Chirobiotic V column (available from Advanced Separation Technologies, Inc.) under the following conditions:

Flow rate: 1.0 mL/min;
Detector: 210 nm;
Mobile phase: isocratic 0.1% Et$_3$n; 0.1% AcOH in MeOH
Retention Times:
   (S)-enantiomer: 14.1 minutes
   (R)-enantiomer: 13.7 minutes

What is claimed is:

1. A process for the preparation of an enantiomerically enriched mixture of a major and minor diatereoisomer compounds of structural formula I:

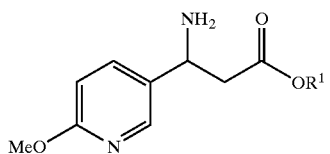

wherein

R$^1$ is C$_{1-4}$ alkyl;

which comprises forming a salt of a compound of formula I with an (R)- or (S)-amino acid of structural formula II:

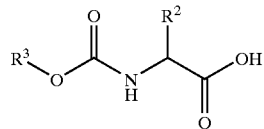

wherein R$^2$ is selected from the group consisting of phenyl, benzyl, 1-naphthylmethyl, 2-naphthylmethyl, 4-imidazolylmethyl, and 4-hydroxybenzyl; and and R$^3$ is tert-butyl, benzyl or 9-fluorenylmethyl.

2. A process for the preparation of an enantiomerically enriched mixture of a major and minor diastereoisomer compounds of structural formula I:

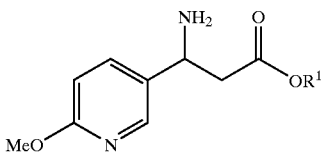

wherein

R$^1$ is C$_{1-4}$ alkyl;

comprising the steps of:
(a) mixing a compound of structural formula I with an (R)- or (S)-amino acid of structural formula II:

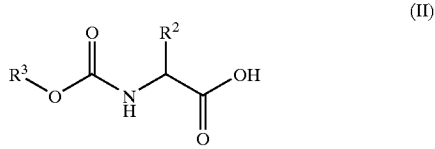

wherein R$^2$ is selected from the group consisting of phenyl, benzyl, 1-naphthylmethyl, 2-naphthylmethyl, 4-imidazolylmethyl, and 4-hydroxybenzyl; and and R$^3$ is tert-butyl, benzyl or 9-fluorenylmethyl; in an alcohol solvent system to form a mixture;

(b) heating the mixture from about 10° C. to about 100° C.;

(c) allowing the mixture to cool so that a crystalline (R)- or (S)-amino acid salt of said compound of formula I is formed;

(d) filtering the mixture to separate the crystalline salt from the supernatant; and (e) liberating said compound of formula I from the crystalline salt by treating the salt with a base.

3. The process of claim 1 wherein R$^1$ is methyl, ethyl, or tert-butyl.

4. The process of claim 1 wherein R$^2$ is benzyl.

5. The process of claim 1 wherein R$^3$ is benzyl.

6. The process of claim 1 wherein R$^2$ and R$^3$ are benzyl.

7. The process of claim 1 wherein the amino acid of structural formula II is N-(benzyloxycarbonyl)-(S)-phenylalanine.

8. The process of claim 2 wherein said alcohol solvent system is aqueous ethanol or aqueous methanol.

* * * * *